(12) United States Patent
Mohl

(10) Patent No.: US 12,419,748 B2
(45) Date of Patent: Sep. 23, 2025

(54) IMPLANT FOR IMPROVING COAPTATION OF AN ATRIOVENTRICULAR VALVE

(71) Applicant: AVVIE GMBH, Vienna (AT)

(72) Inventor: Werner Mohl, Altenmarkt-Thennenberg (AT)

(73) Assignee: AVVIE GMBH, Vienna (AT)

(*) Notice: Subject to any disclaimer, the term of this patent is extended or adjusted under 35 U.S.C. 154(b) by 624 days.

(21) Appl. No.: 17/273,910

(22) PCT Filed: Sep. 4, 2019

(86) PCT No.: PCT/IB2019/057431
§ 371 (c)(1),
(2) Date: Mar. 5, 2021

(87) PCT Pub. No.: WO2020/049466
PCT Pub. Date: Mar. 12, 2020

(65) Prior Publication Data
US 2021/0353418 A1 Nov. 18, 2021

(30) Foreign Application Priority Data
Sep. 7, 2018 (EP) .................................. 18000723

(51) Int. Cl.
*A61F 2/24* (2006.01)
(52) U.S. Cl.
CPC .......... *A61F 2/2463* (2013.01); *A61F 2/2466* (2013.01); *A61F 2/246* (2013.01); *A61F 2210/0014* (2013.01)
(58) Field of Classification Search
CPC ............................... A61F 2/2463; A61F 2/246
See application file for complete search history.

(56) References Cited

U.S. PATENT DOCUMENTS

| | | | |
|---|---|---|---|
| 8,992,605 B2 | 3/2015 | Zakai et al. | |
| 9,510,946 B2 * | 12/2016 | Chau | A61F 2/2457 |

(Continued)

FOREIGN PATENT DOCUMENTS

| | | | | |
|---|---|---|---|---|
| WO | WO-2012035279 A1 * | 3/2012 | ........... | A61F 2/2418 |
| WO | WO-2016110760 A1 * | 7/2016 | ....... | A61B 17/00234 |
| WO | 2017/115123 A1 | 7/2017 | | |

OTHER PUBLICATIONS

International Search Report dated Nov. 14, 2019, issued in corresponding International Patent Application No. PCT/IB2019/057431 (2 pgs.).

(Continued)

*Primary Examiner* — Bruce E Snow
(74) *Attorney, Agent, or Firm* — Pillsbury Winthrop Shaw Pittman, LLP

(57) ABSTRACT

The invention relates to an implant for improving coaptation of an atrioventricular valve in a heart, the atrioventricular valve having a native first leaflet, a native second leaflet and optionally an annulus adjacent a wall of an atrium of the heart, the implant comprising a support structure configured to be arranged on and fixed to the annulus or to at least one of the first and second native leaflets, the implant further comprising retention means fixed to the support structure so as to prevent prolapse of the at least one native leaflet, whereby the support structure comprises a resting element that is configured to rest against the wall of the atrium adjacent the valve.

18 Claims, 10 Drawing Sheets

(56) References Cited

U.S. PATENT DOCUMENTS

| | | | | |
|---|---|---|---|---|
| 2004/0138745 A1* | 7/2004 | Macoviak | ............ | A61F 2/2445 |
| | | | | 623/2.14 |
| 2004/0260393 A1* | 12/2004 | Rahdert | ............ | A61B 17/0401 |
| | | | | 623/2.36 |
| 2015/0230919 A1* | 8/2015 | Chau | .................... | A61F 2/2412 |
| | | | | 623/2.11 |
| 2016/0030176 A1* | 2/2016 | Mohl | ................... | A61F 2/2454 |
| | | | | 623/2.11 |
| 2016/0166382 A1* | 6/2016 | Nguyen | ................. | A61F 2/246 |
| | | | | 623/2.17 |
| 2016/0324639 A1* | 11/2016 | Nguyen | ............... | A61F 2/2409 |
| 2017/0189186 A1* | 7/2017 | Mohl | ................... | A61F 2/2454 |
| 2018/0242976 A1* | 8/2018 | Kizuka | ............... | A61B 17/083 |
| 2024/0197472 A1* | 6/2024 | Bruchman | ............ | A61F 2/2403 |

OTHER PUBLICATIONS

Written Opinion of the International Searching Authority dated Nov. 14, 2019, issued in corresponding International Patent Application No. PCT/IB2019/057431 (5 pgs.).

International Preliminary Report on Patentability dated Oct. 23, 2020, issued in corresponding International Patent Application No. PCT/IB2019/057321 (6 pgs.).

Second Written Opinion of the International Preliminary Examining Authority dated Jul. 16, 2020 issued in corresponding International Patent Application No. PCT/IB2019/057431 (5 pgs.).

Reply to Communication PCT/IPEA/408 dated Sep. 15, 2020 filed in corresponding International Patent Application No. PCT/IB2019/057431 (3 pgs).

Demand and Amended claim sheets dated Jul. 7, 2020 filed in corresponding International Patent Application No. PCT/IB2019/057431 (19 pgs.).

* cited by examiner

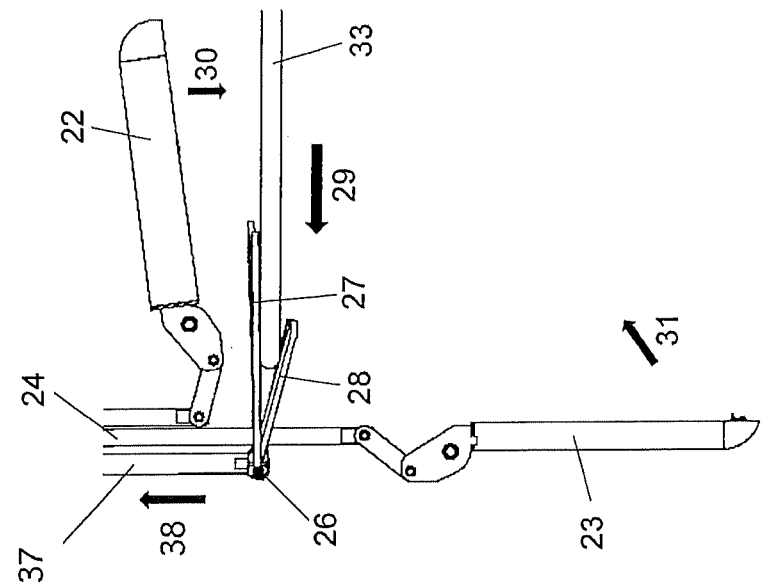
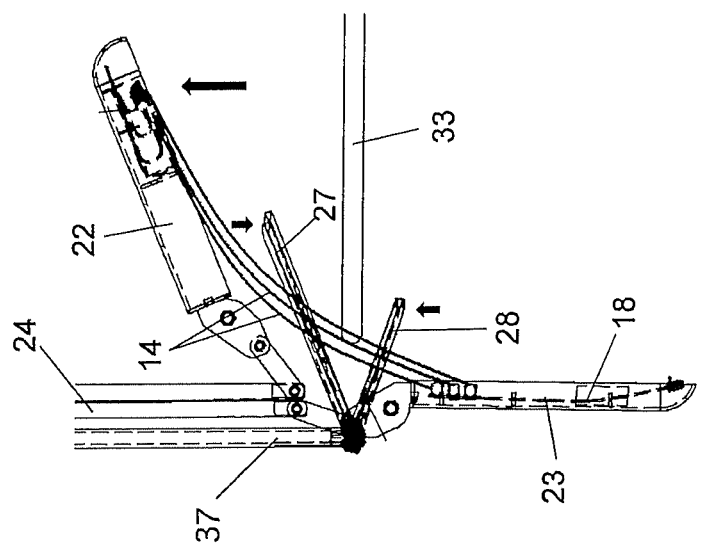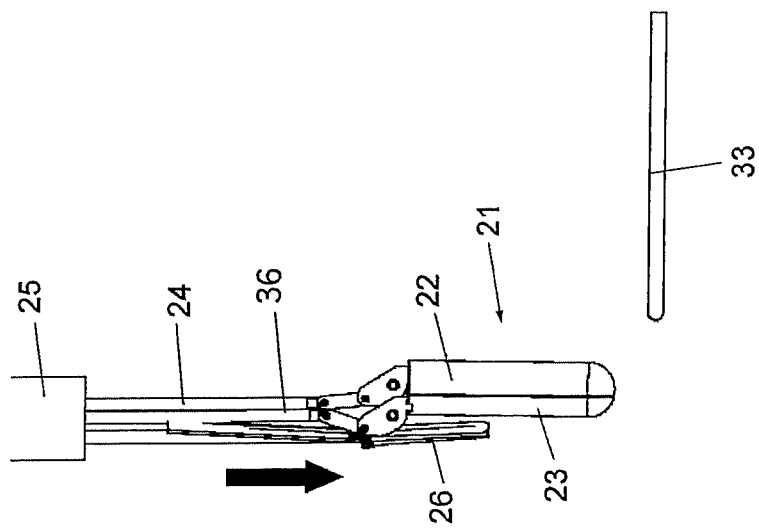

IMPLANT FOR IMPROVING COAPTATION OF AN ATRIOVENTRICULAR VALVE

CROSS-REFERENCE TO RELATED APPLICATIONS

This application is a national stage entry of PCT/IB2019/057431, filed Sep. 4, 2019, which claims priority to European Application No. 18000723.9, filed Sep. 7, 2018, the entire contents of both of which are herein incorporated by reference in their entireties.

The invention relates to an implant for improving coaptation of an atrioventricular valve.

Atrioventricular valves are membranous folds that prevent backflow from the ventricles of the human heart into the atrium during systole. They are anchored within the ventricular cavity by chordae tendineae, which prevent the valve from prolapsing into the atrium.

The chordae tendineae are attached to papillary muscles that cause tension to better hold the valve. Together, the papillary muscles and the chordae tendineae are known as the subvalvular apparatus. The function of the subvalvular apparatus is to keep the valves from prolapsing into the atria when they close. The opening and closure of the valves is caused by the pressure gradient across the valve.

The human heart comprises two atrioventricular valves, the mitral valve and the tricuspid valve. The mitral valve allows the blood to flow from the left atrium into the left ventricle. The tricuspid valve is located between the right atrium and the right ventricle. The mitral valve has two leaflets that are each divided into several scallops: the anterior leaflet has three scallops (A1,A2,A3), the posterior leaflet has three scallops (P1,P2,P3). Furthermore, the mitral valve has an annulus. The tricuspid valve has three leaflets. Engagement of corresponding surfaces of the leaflets against each other is decisive for providing closure of the valve to prevent blood flowing in the wrong direction. The closure forms a so called coaptation area.

Native heart valves become dysfunctional for a variety of pathological causes. Failure of the leaflets to seal during ventricular systole is known as malcoaptation and may allow blood to flow backward through the valve (regurgitation). Malcoaptation is often caused by a dilatation of the annulus. This is mainly due to an enlargement of the left atrium with preserved posterior wall motion or in case of posterior myocardial infarction due to posterior wall motion abnormalities leading to asymmetric annular dilatation. Another reason is a restriction in motion or an excessive motion of the leaflet structures. Another cause of severe regurgitation is the local elongation or rupture of chordae resulting in a prolapse of parts of the leaflet. Heart valve regurgitation can result in cardiac failure, decreased blood flow, lower blood pressure, and/or a diminished flow of oxygen to the tissues of the body. Mitral regurgitation can also cause blood to flow back from the left atrium to the pulmonary veins, causing congestion and backward failure.

Some pathologies of atrioventricular valves, such as malcoaptation, often require reconstruction of the valvular and subvalvular apparatus as well as redesigning the enlarged annulus. Sometimes a complete surgical replacement of the natural heart valve with heart valve prosthesis is necessary. There are two main types of artificial heart valves: the mechanical and the biological valves. The mechanical-type heart valve uses a pivoting mechanical closure supported by a base structure to provide unidirectional blood flow. The tissue-type valves have flexible leaflets supported by a base structure and projecting into the flow stream that function similar to those of a natural human heart valve and imitate their natural flexing action to coapt against each other. Usually two or more flexible leaflets are mounted within a peripheral support structure made of a metallic or polymeric material. In transcatheter implantation the support within the annulus may be in the form of a stent, as is disclosed in US 2011/0208298 A1.

In order to provide enough space for the artificial leaflets to work properly, the peripheral support is positioned in the native valve so as to force the native leaflets apart. To this end and in order to provide appropriate anchoring of the peripheral support within the native valve, the same is fixed to the native leaflets by suitable means. However, in some applications, such as with mitral valves, fixing the peripheral support to the native anterior leaflet and dislocating the same from its natural position may cause an obstruction of the outflow tract and of the aortic valve, which is located in the left ventricle immediately adjacent the anterior leaflet.

The gold standard for treating mitral regurgitation is to repair the mitral apparatus including leaflets and the subvalvular apparatus and to reshape the mitral annulus (Carpentier technique). If repair is not possible an excision of the valve including parts of the subvalvular apparatus is performed with subsequent implantation of a heart valve prosthesis. This is necessary particularly when the valve is destructed by inflammation. Although in most instances a complete excision of the destroyed valve is necessary, sometimes a partial replacement is possible. A clinically used mitral valve restoration system (Mitrofix®) replaces only the posterior leaflet with a rigid prosthesis mimicking a fixed posterior leaflet allowing the natural anterior leaflet to coapt. This prosthesis is also sewn into the position of the destroyed posterior aspect of the annulus. This requires open heart surgery and extended cardiac arrest.

Recent trends focus on less invasive procedures to minimize surgical trauma and to perform transcatheter approaches including transatrial, transaortal or transapical procedures to replace or reconstruct dysfunctional valves thus minimizing the need of or avoiding heart lung machine and cardiac arrest. Whereas this is a common procedure in aortic valves nowadays, only few mitral valve insufficiencies are corrected by percutaneous or transapical procedures. Most of these concepts are redesigning and remodeling artificially the mitral annulus to allow coaptation or to enforce coaptation by fixing both leaflets together with a clip reducing mitral regurgitant flow. Percutaneously or transapically deployed valve prostheses are difficult to anchor due to the special anatomy of the mitral valve and the vicinity of the anterior leaflet to the aortic outflow tract.

The main target in clinical therapy is to restore chordal function in case of a ruptured or elongated chord. There are three types of chords, stay chords, primary chords and secondary chords. Each of these chords are grouped and are fixed on one side to the leaflet and on the other side to the papillary muscle. There are two papillary muscles bearing these chords both from the anterior and posterior leaflet. The hemodynamic force acting on the leaflet during valve closure is counteracted by the chords, so that a sufficiency of the valve is reached. The main target in repairing chordal function is to restore one primary chord at the time and fix it to the muscular part of the left ventricle (i.e. papillary muscle or ventricular wall) with artificial chords mainly made from PTFE or other polymers. These artificial chords can be implanted surgically or percutaneously. The main target is to secure an artificial chord between the leaflet and the myocardium. This may induce early or late failure in constructing mitral function, due to nonphysiological orientation of artificial chords resulting in abnormal force. This is the reason for late ventricular rupture and reappearance of valvular dysfunction.

Hence there is the need to provide improved implants for improving coaptation of an atrioventricular valve and to prevent prolapse of the native leaflet into the atrium. Furthermore, implants that do not involve the risk of stenosis of the aortic valve that can be easily deployed to the target site are needed.

An attempt in providing such an improved implant is disclosed in WO 2017/115123 A1. Said implant exhibits a support structure configured to be arranged on and fixed to the annulus or to the native leaflet and retention means fixed to the support structure so as to prevent prolapse of the leaflet, wherein the support structure comprises an upper support element to be arranged on a superior surface of the annulus or the leaflet and a lower support element to be arranged on an inferior surface of the annulus or the leaflet, whereby the support elements are interconnected while clamping a section of the annulus or the leaflet in between.

However, it was observed that the implant as disclosed in WO 2017/115123 A1 is subjected to high dynamic loads, which may result in a certain instability due to the tilting of the implant as a result of the high dynamic loads acting on the implant, and which may cause the supporting elements to affect the native leaflet in the area, where the support structure rests on the valve.

Therefore, it is an object of the instant invention to provide an improved and stable implant for improving coaptation of an atrioventricular valve and preventing prolapse of the native leaflet into the atrium, while preventing an injury or penetration of adjacent valve or heart tissue.

In order to achieve said object the implant according to the invention comprises a support structure configured to be arranged on and fixed to the annulus or to at least one of the first and second native leaflets, the implant further comprising retention means fixed to the support structure so as to prevent prolapse of the at least one native leaflet, whereby the support structure comprises a resting element that is configured to rest against the wall of the atrium adjacent the valve.

Therefore, the invention provides for an enhanced supporting structure, which comprises a resting element. The resting element provides additional support to the implant, because it is configured to rest against the wall of the atrium adjacent the valve. In this way, the implant is not only supported by its support structure being fixed to the at least one leaflet or the annulus, but additionally by the resting element being supported against the wall of the atrium. Thus, the resting element serves for a higher level of stability, because the implant is better held in place and is better secured against the tilting forces acting upon it by the dynamic pressure changes prevailing within the ventricle.

The invention generally provides improved medical implants and methods for the treatment of regurgitation in atrioventricular valves, in particular mitral valves. In some embodiments, the invention provides a medical implant that provides retention means cooperating with at least one of the first and second native leaflet in order to prevent a prolapse thereof into the atrium. Therefore, the implant assists the function of a damaged or otherwise malfunctional native leaflet. However, the damaged or otherwise malfunctional native leaflet is not physically removed. Rather, the damaged or otherwise malfunctional native leaflet is left in the valve, but is now covered by the retention means.

In order to provide a stable connection between the implant and the valve and to prevent a prolapse of the damaged leaflet into the atrium, the support structure is preferably fixed on the annulus of the native valve or on at least one of the first and second native leaflet. The support structure preferably comprises an upper support element to be arranged on a superior surface of the annulus or of the at least one of the first and second native leaflets and a lower support element to be arranged on an inferior of the first and second native leaflets, the upper and the lower support elements each comprising connection means cooperating with each other for interconnecting the upper and the lower support element while clamping a section of the annulus or of the at least one of the first and second native leaflets between the upper support element and the lower support element. More preferably, at least one connection means comprises a penetrating section configured to penetrate the annulus or the at least one of the first and second native leaflets for being connected with the other connection means, which strengthen the connection between the two elements even more.

In order to allow longstanding stability, a layer of a compressible material, such as a compressible PTFE layer, is interposed between the upper support element or the annulus and the upper surface of the native leaflet in the region of penetration and a disc of PTFE for ingrowth of cells is interposed between the lower support element or the annulus and the lower surface of the native leaflet in the region of penetration. The compressible layer may be designed as a disc surrounding the penetration site. The flexible material may be compressed between the upper support element and the lower support element once these have been connected to each other. In this way the compressible material may compensate for the varying thickness of the native leaflet. A further effect of the compressible layer is that it prevents injury of the native leaflet and that it promotes the ingrowth of cells.

Preferably, the support structure is fixed only to the first native leaflet or the second native leaflet. In case of an implant configured for mitral valves, the first native leaflet is a posterior leaflet of the mitral valve and the second native leaflet is an anterior leaflet of the mitral valve. In case the retention means comprise an artificial leaflet, the latter is preferably configured as an artificial posterior leaflet and replaces and/or supports the function of the native posterior leaflet. The artificial posterior leaflet is preferably shaped such as to improve coaptation with the native anterior leaflet and may be adjusted individually based on patient-specific image data obtained by imaging techniques.

In case of an implant configured for tricuspid valves, the first native leaflet is an anterior leaflet of the tricuspid valve and the second native leaflet is a posterior leaflet and the third leaflet is the septal leaflet of the tricuspid valve. In case the retention means comprise an artificial leaflet, the latter is configured to replace the function of the native anterior or posterior leaflet. The artificial anterior or posterior leaflet or the combination of both is preferably shaped such as to improve coaptation with the native anterior and posterior leaflet.

The support structure is preferably fixed only to one leaflet, either the first or the second leaflet, or only to that partial region of the annulus, from which the first or the second leaflet emerges. Further, the retention means are configured to cooperate with and prevent prolapse of only the leaflet, to which the support structure is fixed.

Preferably the resting element has a wing-like structure and preferably is made of wire made of a shape-memory alloy, such as, e.g., nitinol. If stress of varying intensity caused by the blood flow and the blood pressure acts on the valve, the implant tends to swing back and forth. In order to reduce such swinging movement, the resting element is configured to be held in tight contact with the wall of the atrium during the swinging movement. Further, the resting element is preferably connected to the support structure by means of an essentially rigid connection, without any hinge mechanism being provided.

The implant preferably acts like a swing that swings back and forth, whereby the forth movement is stopped when the resting element reaches the atrial wall.

Since the wing-like structure serves for an adequate large area of support in the region where the resting element rests against the wall of the atrium, the load acting on the wall is distributed over a larger area, so that the risk of injuries is reduced, and a punctual penetration of the heart tissue can be effectively prevented. In order to further reduce the risk of injuries, the resting element is preferably provided with a load-distributing element on its side that faces the wall of the atrium. The load-distributing element may be configured as a planar lining or cushion-like element extending over the entire area of the resting element. Said cushion-like element might be expandable, built as a balloon or a gel-cushion.

Since the atrial wall exhibits a beveled shape, the resting element is preferably arranged in a plane that encloses an angle of 90-135° with the plane of the upper support element. Hence the contacting surface between the implant and the atrial wall is optimized.

Preferably the resting element can be incorporated in the native heart tissue. If the resting element is incorporated in the tissue, excess movement of the implant should be avoided in order not to loosen up the contact between the implant and the native tissue. Excess movement can preferably be avoided via an intermediate joint between the resting element and the support structure, which shows very little flexibility. Thereby tissue ingrowth of the resting element is allowed.

In a preferred embodiment the support structure, the resting element and the retention means are deployable from a first position, in which the support structure and the retention means are folded for being arranged within a tubular housing of a delivery device, into a second position, in which the support structure, the resting element and the retention means are deployed. Thereby, the implant can be easily deployed to the heart by minimal invasive surgery or endovascular approaches. In particular, the tubular housing is preferably advanced into the heart by means of a catheter or a deployment instrument transatrially, transseptally, transfemorally or transapically.

Preferably, the support structure, the resting element and the retention means are configured to be deployed from a folded or rolled-up state into an extended state. In the folded or rolled-up state, the structures may easily be advanced to the heart transcatheterally or transapically.

The tubular housing may comprise two half-shells, a first half-shell housing the upper support element and the resting element and a second half-shell housing the lower support element.

Alternatively, the tubular housing may comprise more than two shells, each extending over a segment of the circular cross section of the tubular housing and together forming the tubular housing.

The configuration of the tubular housing with two or more shells allows for a selective deployment of a corresponding number of elements of the implant. A preferred way of deploying the elements of the implant is achieved by having the shells, in particular the first and second half-shells, arranged to swing open. The swinging open of the shells allows to open the tubular housing for enabling a deployment of the implant.

The upper and the lower support elements of the implant may be housed in the tubular housing in a separate, not interconnected manner. Thus, the upper and the lower support elements, each preferably arranged in an own shell of the tubular housing, can easily be deployed separately and be separately brought in the correct position that subsequently allows their connection with each other.

Preferably, the first and second half-shells may be arranged at the distal end of a deployment instrument, such as a steerable instrument or a catheter. The instrument may have a catheter-like tube that may be advanced transapically, transaortically or transatrially into the heart and that carries the tubular housing on its distal end. The proximal end of the deployment instrument, which is held by the surgeon or interventionist, may preferably be provided with actuation means cooperating with the shells of the tubular housing and with the upper and the lower support structure in order to control the swinging open of the shells and of the displacement, the deployment and the extension of the support elements.

In addition, the deployment instrument may be equipped with grasping means, which are arranged at the distal end of the deployment instrument and the proximal end of the half-shells. The grasping means may cooperate with actuation means and serve to grab the tissue on which the implant is to be fixed, i.e. the annulus or one of the leaflets of a heart valve, prior to the implant's deployment. With the aid of said grasping means a fixation of the heart tissue is achieved in the best position needed for fixation of the implant.

The grasping means preferably comprise an upper grasper and a lower grasper, which are arranged to move towards each other in order to grab the native leaflet between them. The upper and the lower graspers are preferably connected by a hinge.

To provide independent actuation and movement of the grasping means relative to the half-shells, the first and the second half-shell are preferably arranged at the distal end of a first steerable part of the deployment instrument and the grasping means are arranged at the distal end of a second steerable part of the deployment instrument.

Prior to fixing the implant, the leaflet has to be stabilized and the site of the leaflet on which the implant is to be fixed, e.g. the site near the hinge between the leaflet and the annulus, has to be brought in the desired position between the half-shells.

The stabilization of the leaflet is achieved by actuating the second steerable part of the deployment instrument, whereby the grasping means are arranged such that the leaflet is enclosed by the upper graspers on its superior surface and the lower graspers on its inferior surface.

In a further step the correct positioning of the grabbed leaflet is achieved by moving the second steerable part of the deployment instrument towards its distal end, which provides for movement of the grasping means and the grabbed leaflet relative to the shells.

Afterwards the first steerable part of the deployment instrument is actuated, whereby the first and the second half shell move towards the leaflet thereby enclosing the same. Then the upper and the lower support structure penetrate the leaflet and are interconnected, whereby fixation of the implant to the heart tissue is achieved. The individual shells of the tubular housing may additionally be constructed so as to be displaceable relative to each other, which facilitates the deployment of the implant even more.

Preferably, the support structure, in particular the lower support element, carries a holding element for holding the retention means. The holding element may preferably be configured as a flexible element that may bend under the load exerted by the blood pressure on the leaflet or the retention element.

In order to mimic the native papillary muscle, the holding element according to a preferred embodiment comprises at least one holding arm, more preferably two holding arms, the region of which that is distal from the lower support element comprises a number of fixing means for fixing the retention means. Preferably, the retention means, on one end thereof, are connected to the upper support element or the resting element and, on the other end thereof, are connected to the holding element. The holding element is thereby built strong enough to counteract the force acting upon the implant and provides a counterpart to the resting element, whereby those parts as well as the retention means fixed thereto are stabilized when stress occurs.

Preferably the retention means comprise a flexible net or a plurality of flexible wires or yarns or a fabric. The flexible net or the plurality of flexible wires or yarns or the fabric cover an area that substantially corresponds to the area of the native leaflet and/or the artificial leaflet to be held by the retention means. The retention means might also be built as a flat sheet, preferably as PTFE sheet or matrix. The PTFE matrix is built by weaving of PTFE yarns or stamping out a flat sheet. The flat sheet option is laminated or tied to the upper support element or the resting element and the holding element. Due to its woven yarns the sheet provides a structured skeleton, which mimics the chordae tendineae, and hence serves for an improved anatomical behavior of the implant. Preferably, a potential ingrowth of cells is promoted in order to achieve a long lasting stability.

Preferably, the flat sheet is made of a woven fabric, wherein the fabric is preferably made from PTFE yarn Alternatively, the flat sheet can be made of an embroidery, wherein an embroidery is stitched onto a polymer substrate that is then removed or dissolved, leaving back the embroidery.

Preferably, a transverse stabilizing element, such as a wire or a nitinol bar, is incorporated into the retention means, in particular the flat sheet, near the coaptation line, in order to spread the retention means over the entire prolapsing segment. Alternatively or additionally, the stabilizing effect may also be achieved by means of the yarns of a woven material of the flat sheet crossing each other.

In order to even better distribute the forces acting on the implant and to optimize the coverage of the area, which is normally covered by the native leaflet, the plurality of flexible wires or yarns preferably comprises a first group of wires or yarns and a second group of wires or yarns, wherein the wires or yarns of the first group are crossing the wires or yarns of the second group.

Preferably, the retention means are fixed on circular type fixing means arranged on the upper support element or the resting element having a wing-like structure and on the holding element, respectively.

More preferably, the atrioventricular valve is a mitral valve and the at least one native leaflet is a posterior or an anterior leaflet of the mitral valve.

In order to enable the resting element to return to its original shape along with the entire implant, and to hence serve for a long living and functioning implant the support structure, the resting element, the holding element and the circular type fixing means may preferably be made of a shape-memory alloy, such as, e.g., nitinol.

According to a preferred embodiment the resting element having a wing-like structure comprises a plurality of wires extending over the length of the resting element and being arranged in a spaced relationship to each other, which serves for a large contact surface between the resting element and the heart tissue, while minimizing material usage. Due to that said configuration also serves for an optimized foldability and hence also an optimized deployability of the implant.

In the following the present invention will be described by reference to some exemplary embodiments.

FIG. 12*a* to 12*f* are schematic illustrations of the consecutive steps of deploying and fixing the implant to the mitral valve.

Figure 12F:
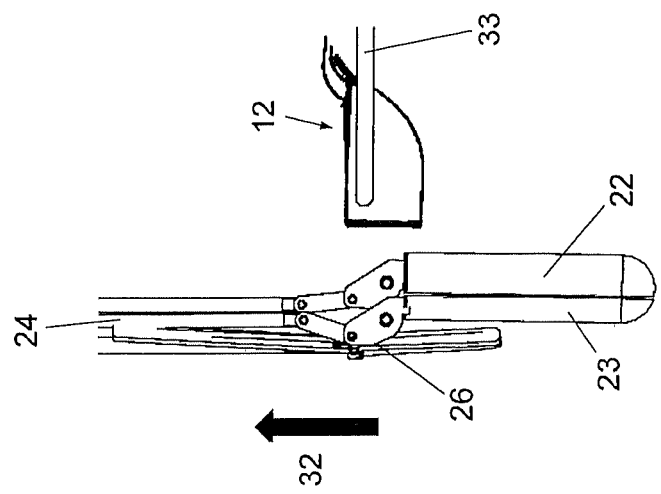
Figure 12E:
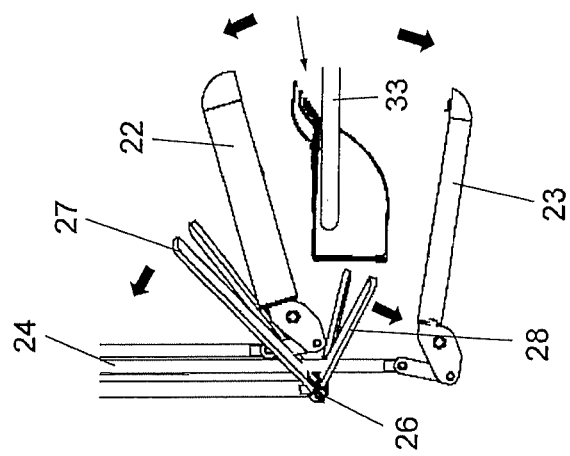
Figure 12D:
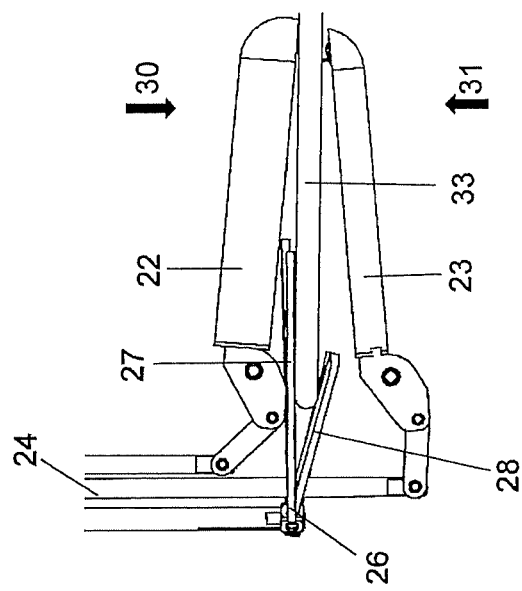
Figure 13:
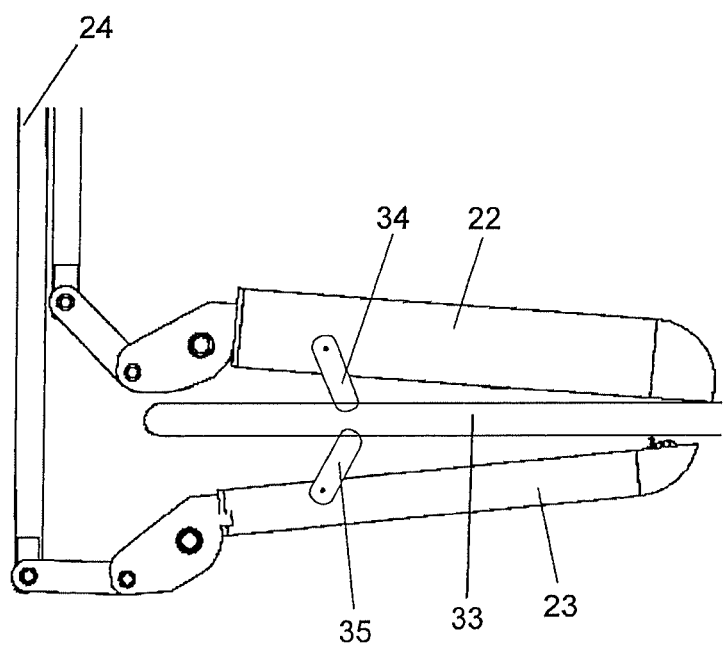

FIG. 13 shows step FIG. 12*d* with an alternative embodiment of the grasping elements.

Figure 1:
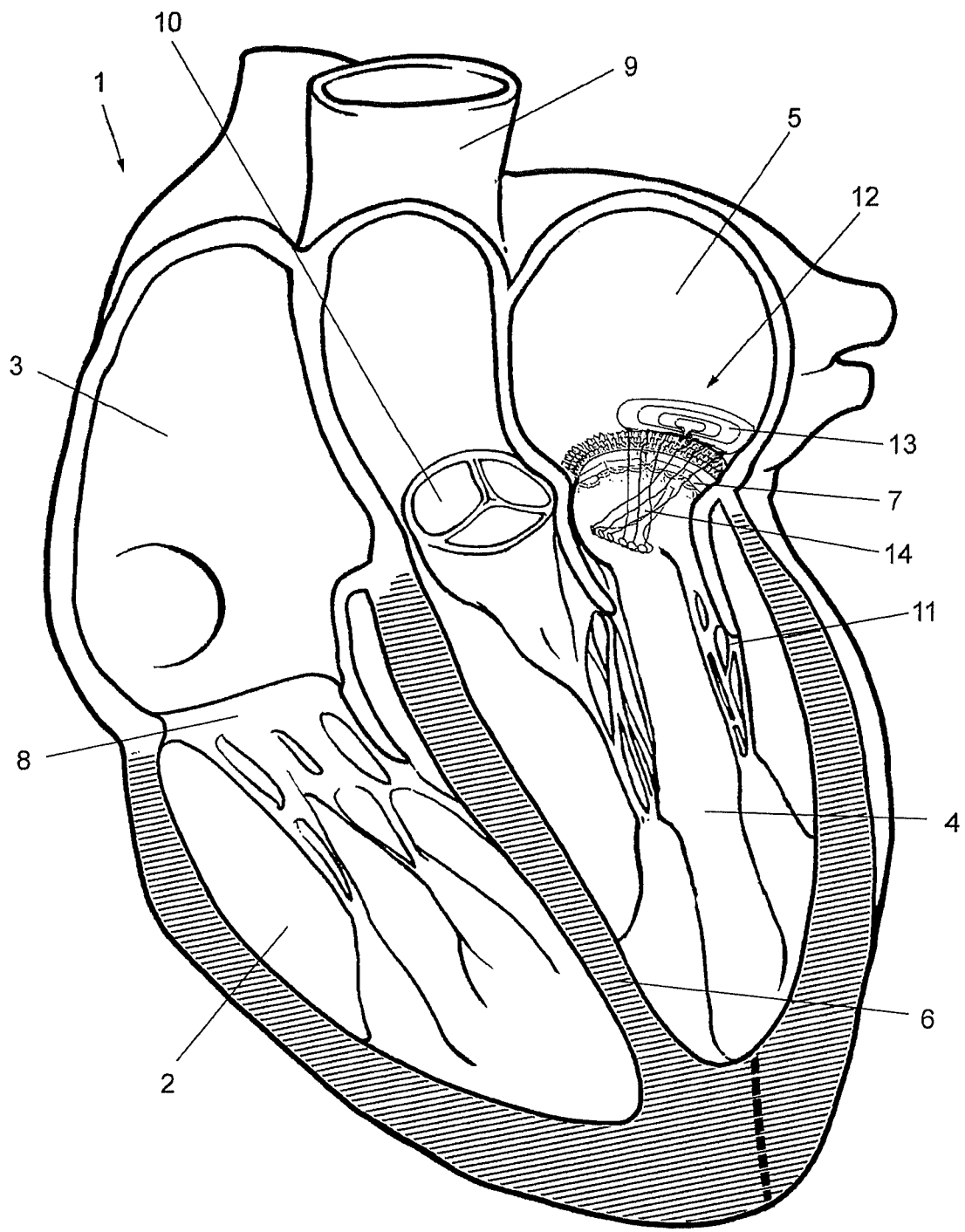
FIG. 1 is a schematic illustration of a human heart with the implant according to a first embodiment of the invention fixed to the mitral valve.

FIG. 1 shows a schematic illustration of a human heart 1 comprising the right ventricle 2, the right atrium 3, the left ventricle 4 and the left atrium 5. The septum 6 divides the heart 1 in a right and a left section. The mitral valve 7 allows the blood to flow from the left atrium 5 into the left ventricle 4. The tricuspid valve 8 is located between the right atrium 3 and the right ventricle 2. The ascending aorta 9 originates at the orifice of the aortic valve 10. The mitral valve 7 comprises an anterior leaflet and a posterior leaflet that are anchored within the left ventricular cavity by chordae tendineae 11, which prevent the valve 7 from prolapsing into the left atrium 5. Furthermore, FIG. 1 shows the implant 12 according to a first embodiment of the invention as being fixed to the posterior leaflet of mitral valve 7, whereby the resting element 13 of the implant 12 rests against the wall of the left atrium 5. The retention means 14 of the implant 12 extend into the left ventricle 4 and cooperate with the posterior leaflet of mitral valve 7 thereby preventing its prolapse.

Figure 2:
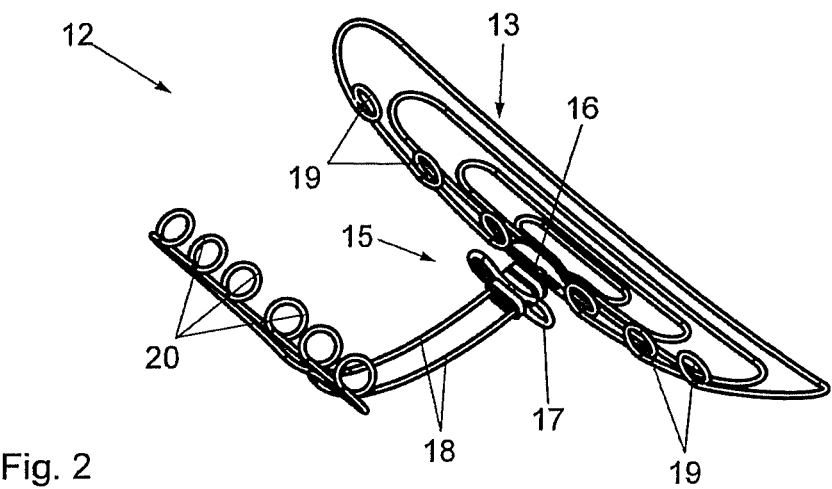
FIG. 2 is a perspective view of the implant according to a first embodiment of the invention.

FIG. 2 is a perspective view of the implant according to a first embodiment of the invention. The implant for improving coaptation of the mitral valve is denoted by 12. The implant 12 comprises a support structure 15, retention means (not shown), which are fixed to the support structure 15, and a resting element 13. The support structure 15 comprises an upper support element 16 and a lower support element 17. The lower support element 17 carries a holding element 18 for holding the retention means 14 on one end thereof, whereby the retention means 14, on the other end thereof, are connected to the resting element 13. The retention means 14 comprise two groups of yarns crossing each other, which are fixed to circular type fixing means 19,20 arranged on the resting element 13 and on the holding element 18, respectively.

When being implanted to the posterior leaflet 33 of the mitral valve 7 of a human heart 1 the upper support element 16 is arranged on the superior surface of the posterior leaflet 33 of the mitral valve 7 and the lower support element 17 is arranged on the inferior surface of the posterior leaflet 33 of the mitral valve 7, whereby the upper support element 16 and the lower support element 17 cooperate which each other and thereby clamp the posterior leaflet in between and the implant 12 is hence fixed to the posterior leaflet 33. When being implanted the resting element 13 rests against the wall of the left atrium 5 adjacent the posterior leaflet 33 of the mitral valve 7 and the retention means 14, which are fixed to the support structure 15 of the implant 12, extend to the left ventricle 4 and thereby prevent prolapse of the posterior leaflet 33 of the mitral valve 7.

Figure 3:
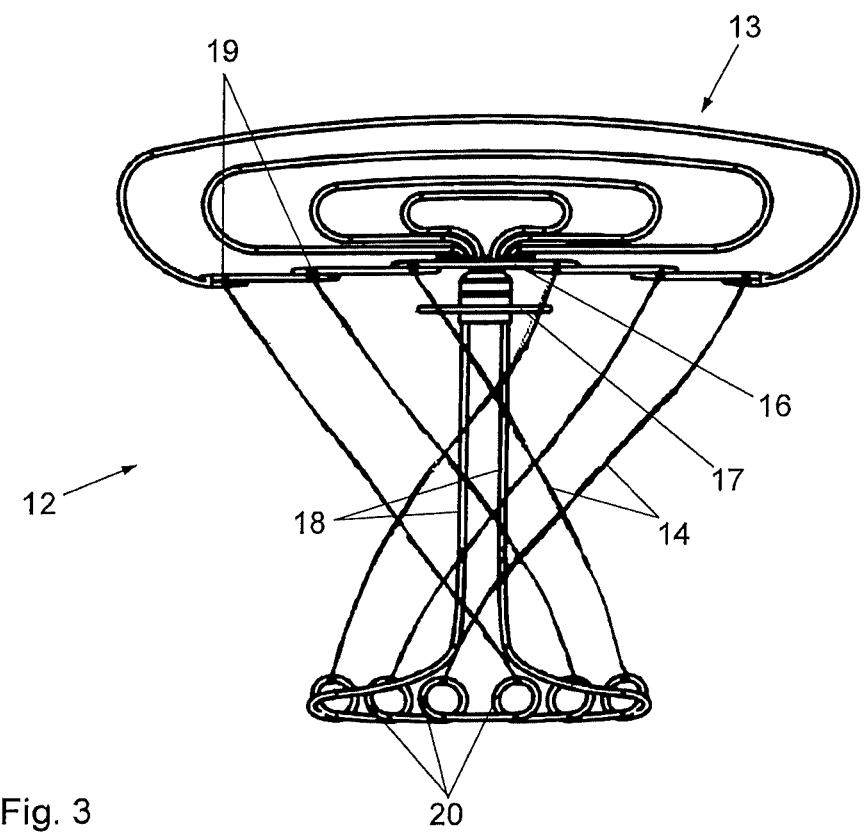
FIG. 3 is a front view of the implant of FIG. 2.
Figure 4:
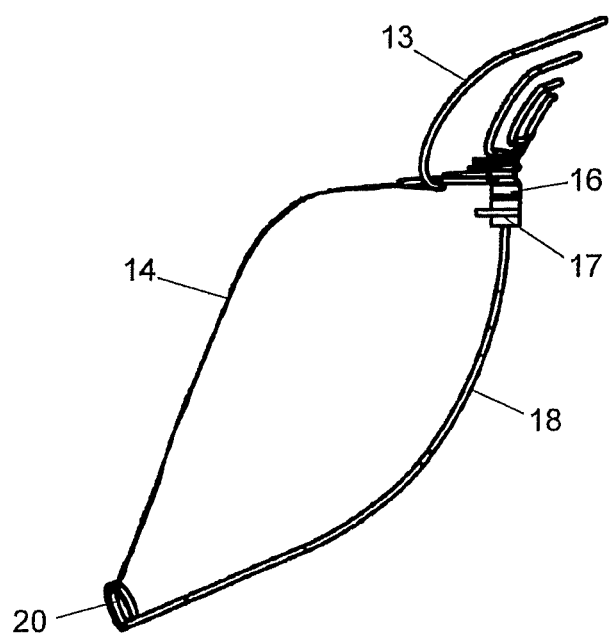
FIG. 4 is a side view of the implant of FIG. 2.
Figure 5:
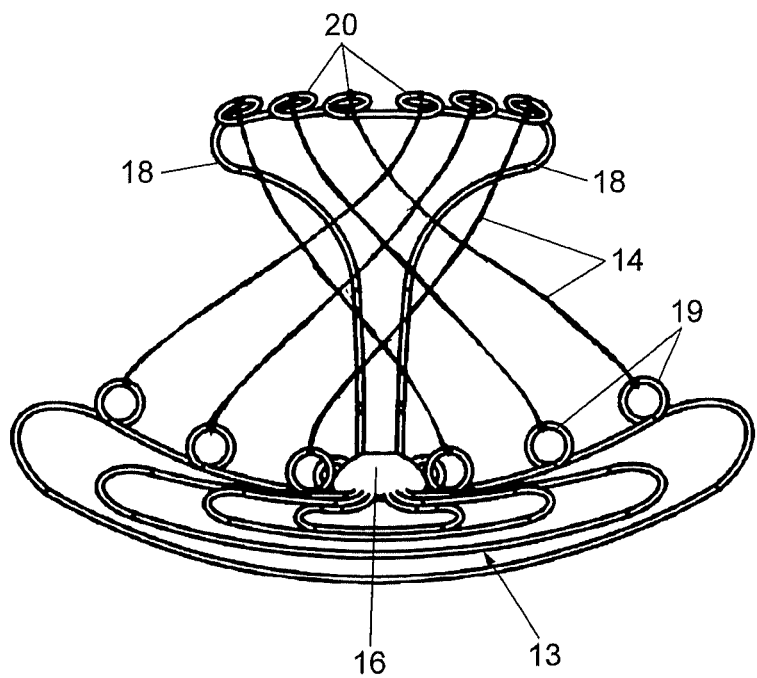
FIG. 5 is a top view of the implant of FIG. 2.

FIG. 3 is a front view of the implant 12 of FIG. 2, FIG. 4 is a side view and FIG. 5 is a top view of the implant 12 of FIG. 2, whereby the same reference numerals as used in FIG. 2 are used for denoting the individual components of the implant 12.

Figure 6:
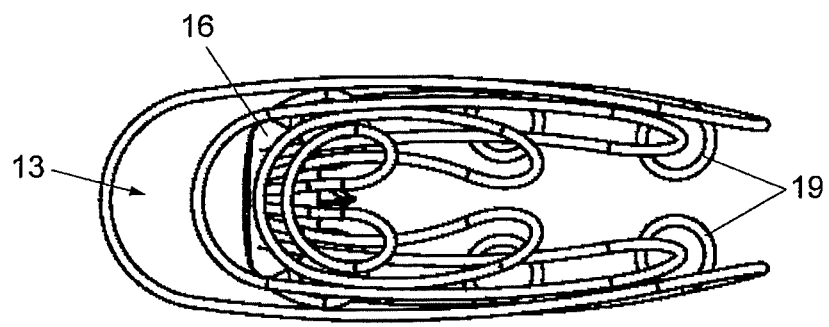
FIG. 6 shows an upper part of the implant of FIG. 2 in a folded state.
Figure 7:
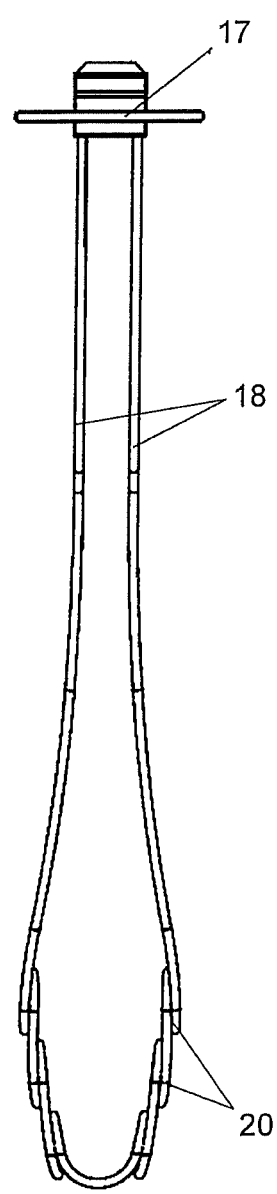
FIG. 7 shows a lower part of the implant of FIG. 2 in a folded state.

For being delivered to the heart percutaneously, the implant 12 is folded in order to be housed in an elongate tubular housing of delivery device. FIG. 6 shows the upper part of the implant, comprising the upper support element 15 and the resting element, in its folded state. FIG. 7 shows the lower part of the implant 12, comprising lower support element 17 and the holding element 18, in its folded state.

Figure 8:
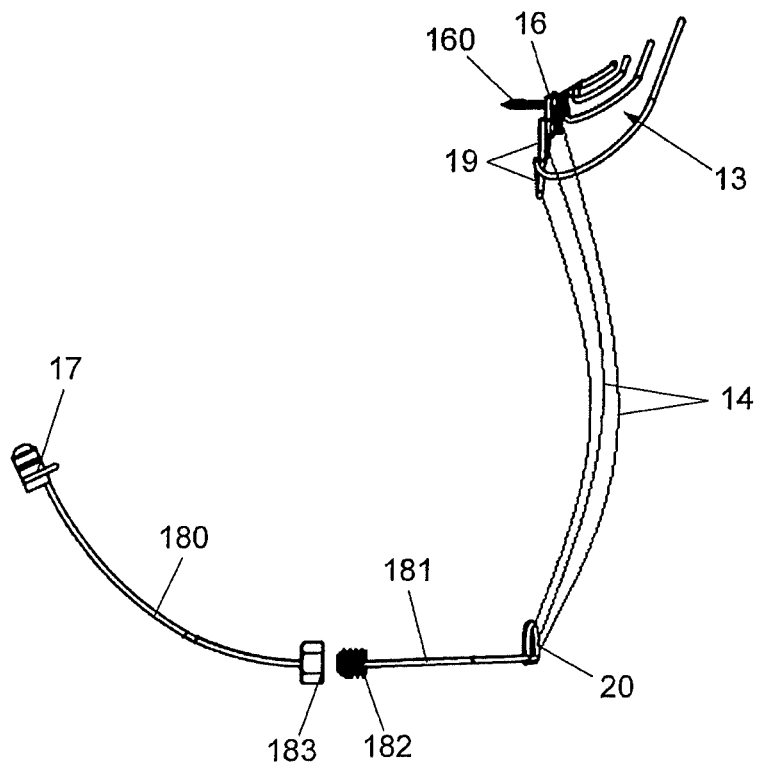
FIG. 8 is a side view of the implant according to a second embodiment of the invention.
Figure 9:
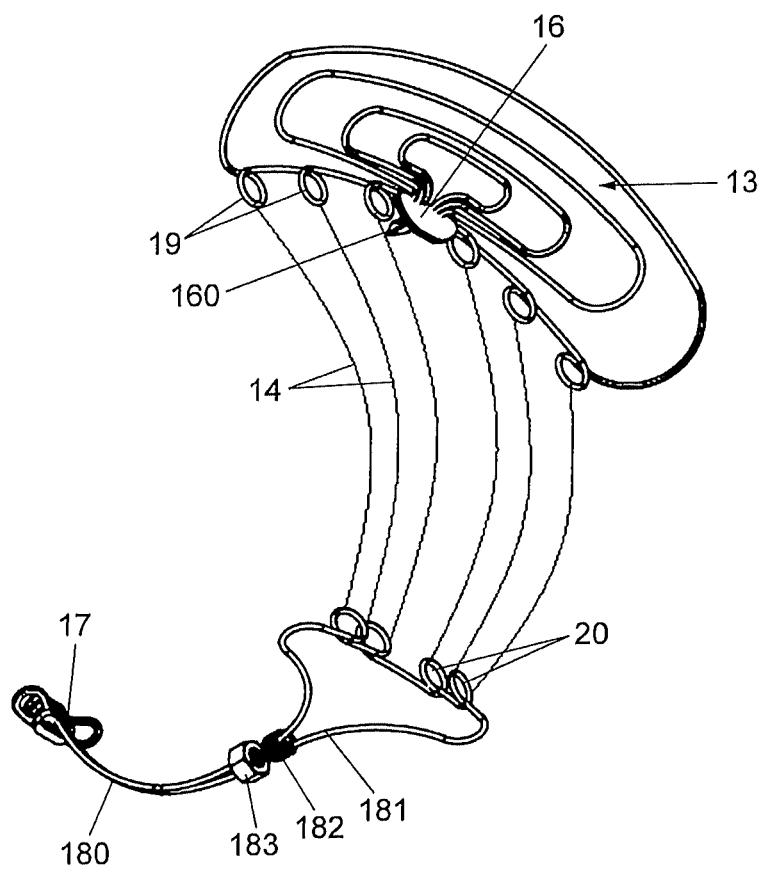
FIG. 9 is a perspective view of the implant of FIG. 8.

FIGS. 8 and 9 illustrate a second embodiment of the implant 12, which essentially corresponds to the first embodiment, but the holding element 18 of which is divided in two parts 180 and 181 that are detachable. The two parts 180 and 181 can be connected with each other with a screw connection consisting of a screw element 182 and a screw nut element 183. During production of the implant, the part 180 is detached from the part 181 so as to allow the implant 12 to be mounted on a stitching machine, that is used to manufacture the retention means 14 as an embroidery directly onto the implant 12.

Further, in FIGS. 8 and 9 the implant 12 is shown with the lower support element 17 detached from the upper support element 16 so that the connection means for connecting the two support elements with each other are partly visible. In particular, the upper support element 16 comprises a penetration needle 160 that penetrates the leaflet 33 of the mitral valve when the upper support element 16 and the lower support element 17 are clamped together for being interconnected.

Figure 10:
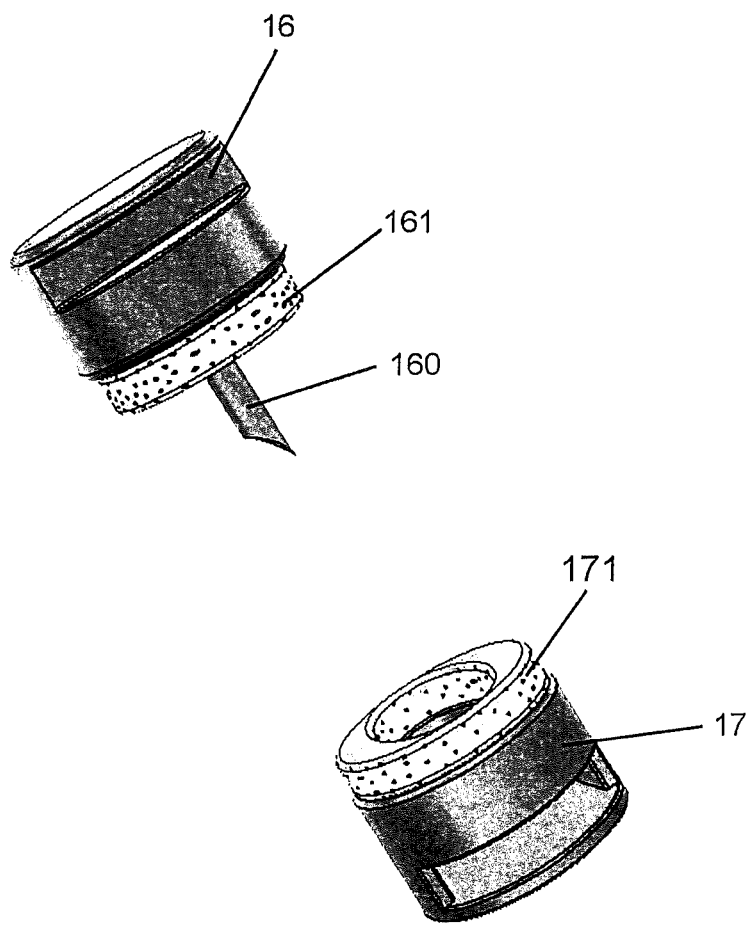
FIG. 10 shows the connection means optionally used in the implant of FIGS. 2-9.

FIG. 10 shows the connection means of the support elements 16 and 17 in more detail. In particular, the upper support element 16, on its side facing the leaflet, carries a compressible layer or ring 161, which can be made of, e.g., PTFE. The lower support element 17, on its side facing the leaflet, carries a compressible layer or ring 171, which can be made of, e.g., PTFE. Thereby necrosis and/or apoptosis of the tissue between the upper and the lower support element may be avoided.

Figure 11:
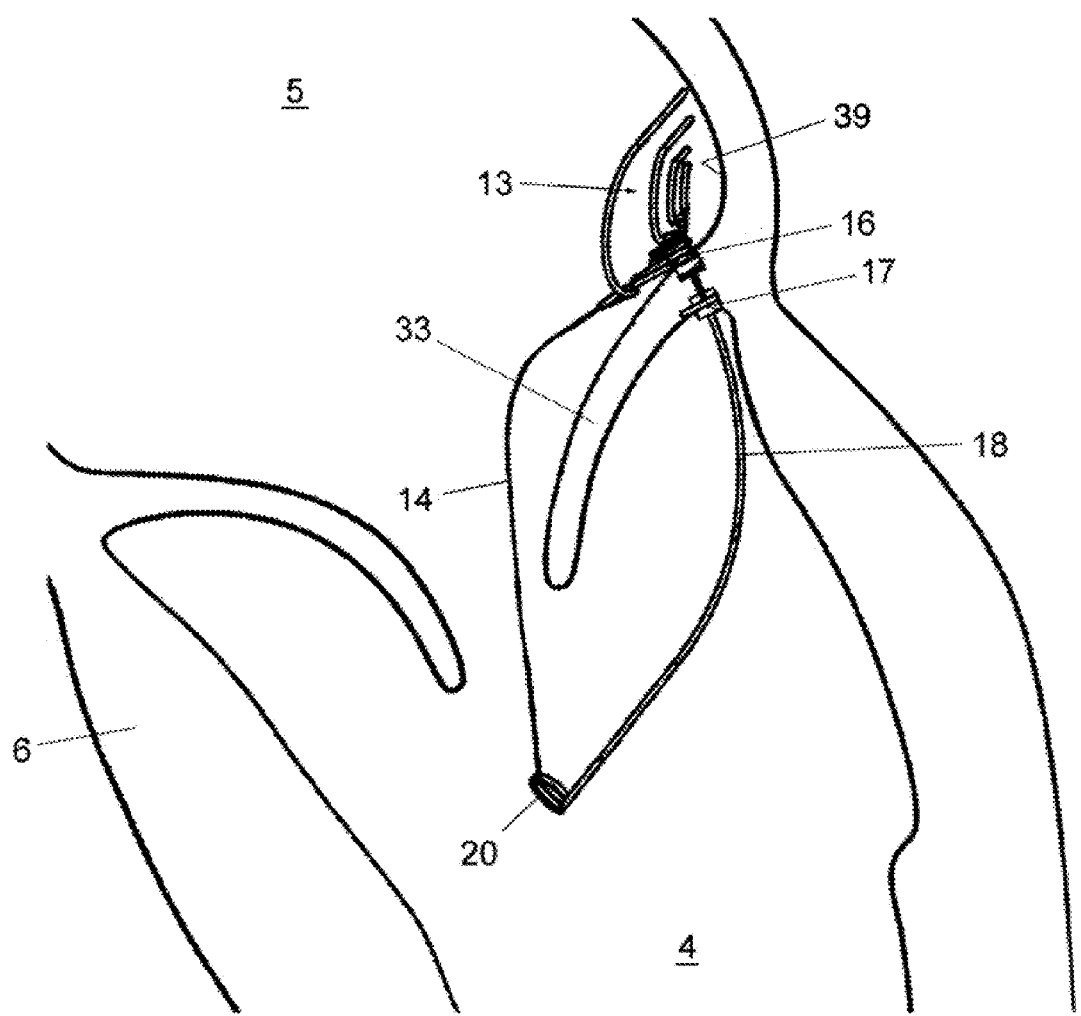
FIG. 11 shows the implant of FIG. 2 when fixed to a leaflet of a mitral valve.

FIG. 11 schematically illustrates the implant 12 when being implanted. As can be seen, the retention means 14 is fixed to the holding arms 18 of the lower support element 17 and on the upper support element 16 and, between these fixing points, provides a structure that retains the leaflet 33 of the mitral valve 7 so as to prevent a prolapse. In order to prevent the implant 12 from excessively swinging into the left atrium 5 as a result of the dynamic pressure changes prevailing within the ventricle, the resting element 13 is arranged to rest against the wall 39 of the left atrium 5 adjacent the posterior leaflet 33.

FIG. 12a to 12f are schematic illustrations of the consecutive steps of deploying and fixing the implant to the heart tissue.

In order to advance the implant 12 to the mitral valve 7, the implant is in the first implanting step as depicted in FIG. 12a arranged in a tubular housing 21, which comprises a first half-shell 22 and a second half-shell 23, whereby the first half-shell 22 houses the upper part of the implant 12, i.e. the upper support element 16 and the resting element 13, and the second half-shell 23 houses the lower part of the implant 12, i.e. the lower support element 17 and the holding element 18 (cf. FIG. 12b). The first and the second half-shells 22,23 are arranged at the distal end of a first steerable part 36 of a deployment instrument 24, which is surrounded by a catheter-like tube 25 that may be advanced transapically, transaortically or transatrially into the heart. The deployment instrument 24 is further equipped with grasping means 26, which are arranged at the distal end of a second steerable part 37 of the deployment instrument 24. The grasping means 26 comprise an upper grasper 27 and a lower grasper 28, which are connected by a hinge.

As can be taken from FIG. 12b actuation means (not shown), which are arranged on the proximal end of the deployment instrument 24, induce the upper and the lower shells 22,23 of the tubular housing 21 to swing open and to unfold the upper and the lower graspers 27,28 of the grasping means 26 so as to unfold the retention means 14, which connect the upper part of the implant to the lower part of the implant.

In a first step the grasping means 26 are arranged such that the posterior leaflet 33 of mitral valve 7, on which the implant is to be fixed, is enclosed by the upper graspers 27 on its superior surface and the lower graspers 28 on its inferior surface, thereby holding the posterior leaflet 33 in place. To arrange the leaflet 33 in the desired position prior to fixing of the implant, i.e. between the upper shell 22 and the lower shell 23, the leaflet 33, which is grabbed between the upper and the lower graspers is pulled towards the distal end of the deployment instrument 24 according to arrow 29 by moving the second steerable part 37 of the deployment instrument 24 according to arrow 38. In a further step the first steerable part 36 of the deployment instrument 24 is actuated, whereby the first and the second half shell 22,23 move towards the posterior leaflet 33 according to arrows 30 and 31 and grab the same in between (cf. FIG. 12c and 12d). When the first and the second half shells 22,23 fully enclose the posterior leaflet 33 of the mitral valve 7, the upper and the lower support structure 16,17 of the implant 12 penetrates the leaflet 33, whereby the upper and the lower support element (not shown) of the implant interconnect.

In a next step (cf. FIG. 12e) the first and the second half shell 22,23 of the tubular housing 21 are opened thereby moving away from the posterior leaflet 33 and releasing the implant, which unfolds upon release and hence achieves its final state of implantation. After successful implantation of the implant 12 the deployment instrument 24 is retracted from the implantation site, whereby half shells 22 and 23 are shut and the deployment instrument 24 is moved backwards according to arrow 32 in order to be withdrawn from the heart (cf. FIG. 12f).

FIG. 13 shows an alternative embodiment of the delivery device, wherein the grasping means are replaced by clamping elements 34 and 35 that are pivotally connected to the upper and the lower shells 22,23 and are used to clamp the leaflet 33 between them to hold it in a suitable position, while the upper and the lower shells 22,23 are placed to position the lower and the upper supporting elements of the implant as close as possible to the annulus.

The invention claimed is:

1. An implant for improving coaptation of an atrioventricular valve in a heart, the atrioventricular valve having a native first leaflet, a native second leaflet and an annulus adjacent a wall of an atrium of the heart, the implant comprising a support structure configured to be arranged on and fixed to the annulus or to at least one of the first and second native leaflets, wherein the support structure comprises an upper support element to be arranged on a superior surface of the annulus or of the at least one of the first and second native leaflets and a lower support element to be arranged on an inferior surface of the annulus or of the at least one of the first and second native leaflets, the upper and the lower support elements each comprising connection means cooperating with each other for interconnecting the upper and the lower support elements while clamping a section of the annulus or of the at least one of the first and second native leaflets between the upper support element and the lower support element along a clamping plane of the upper and lower support elements, the implant further comprising retention means fixed to the support structure so as to prevent prolapse of the at least one of the first and second native leaflets, characterized in that one of the first and second native leaflets is a posterior leaflet, the support structure comprises a resting element that is configured to rest against the wall of the atrium adjacent the posterior leaflet along a resting plane and thereby prevent said prolapse in combination with the retention means while still allowing swing movement of the posterior leaflet, wherein the lower support element carries a holding element for holding the retention means, and wherein an angle of 90-135° is provided within the atrium between the resting plane and the clamping plane of the upper and lower support elements.

2. The implant of claim 1, wherein at least one of the connection means comprises a penetrating section configured to penetrate the annulus or the at least one of the first and second native leaflets for being connected with the other connection means.

3. The implant of claim 1, wherein the resting element has a wing-like structure and is made of wire made of a shape-memory alloy.

4. The implant of claim 1, wherein the support structure, the resting element and the retention means are deployable from a first position, in which the support structure and the retention means are folded for being arranged within a tubular housing of a delivery device, into a second position, in which the support structure, the resting element and the retention means are deployed.

5. The implant of claim 1, wherein the holding element comprises at least one holding arm, a region of which that is distal from the lower support element comprises a number of fixing means for fixing the retention means.

6. The implant of claim 1, wherein the retention means, on one end thereof, are connected to the upper support element or the resting element and, on the other end thereof, are connected to the holding element.

7. The implant of claim 1, wherein the retention means comprises one of: a flexible net, a plurality of flexible wires or yarns, a fabric, and a flat sheet.

8. The implant of claim 7, wherein the retention means comprises the plurality of flexible wires or yarns, wherein the plurality of flexible wires or yarns comprises a first group of wires or yarns and a second group of wires or yarns, wherein the wires or yarns of the first group are crossing the wires or yarns of the second group.

9. The implant of claim 1, wherein the retention means are fixed on circular type fixing means and on the holding element, respectively, whereby the circular type fixing means are arranged on the upper support element or the resting element, and wherein the resting element has a wing-like structure.

10. The implant of claim 1, wherein the atrioventricular valve is a mitral valve.

11. The implant of claim 9, wherein the support structure, the resting element, the holding element and the circular type fixing means are made of a shape-memory alloy.

12. The implant of claim 3, wherein the resting element having the wing-like structure comprises a plurality of wires extending over a length of the resting element and arranged in a spaced relationship to each other.

13. A system for deploying, comprising a deployment instrument with a tubular housing and the implant according to claim 1, wherein the tubular housing comprises two half-shells, a first half-shell housing the upper support element and the resting element, and a second half-shell housing the lower support element.

14. The system of claim 13, wherein the first and the second half-shells are arranged at a distal end of the deployment instrument.

15. The system of claim 13, wherein the first and the second half-shells are arranged to swing open in order to allow the implant to be deployed.

16. The system of claim 13, wherein the deployment instrument further comprises grasping means, which are arranged at a distal end of the deployment instrument and a proximal end of the first and second half-shells.

17. The system of claim 16, wherein the grasping means comprise an upper grasper and a lower grasper, which are arranged to move towards each other in order to grab the corresponding native first or second leaflet between them.

18. The system of claim 16, wherein the first and the second half-shells are arranged at a distal end of a first steerable part of the deployment instrument and the grasping means are arranged at a distal end of a second steerable part of the deployment instrument in order to be movable independently from each other.

\* \* \* \* \*